United States Patent
Mendelewicz et al.

(10) Patent No.: US 10,814,132 B2
(45) Date of Patent: Oct. 27, 2020

(54) RETINAL IMPLANT WITH INSERTION CORD

(71) Applicant: NANO-RETINA LTD., Herzeliya (IL)

(72) Inventors: Rani Mendelewicz, Herzeliya (IL); David Rigler, Kadima-Tzoran (IL); Yaakov Milstain, Zichron-Yaakov (IL); Dorit Raz Prag, Pardes Hanna-Karkur (IL)

(73) Assignee: NANO RETINA LTD., Herzeliya (IL)

( * ) Notice: Subject to any disclaimer, the term of this patent is extended or adjusted under 35 U.S.C. 154(b) by 93 days.

(21) Appl. No.: 16/259,611

(22) Filed: Jan. 28, 2019

(65) Prior Publication Data

US 2019/0151662 A1    May 23, 2019

Related U.S. Application Data

(63) Continuation of application No. 15/342,765, filed on Nov. 3, 2016, now Pat. No. 10,226,625.

(51) Int. Cl.
*A61N 1/36* (2006.01)
*A61F 9/00* (2006.01)
*A61N 1/05* (2006.01)
*A61N 1/372* (2006.01)

(52) U.S. Cl.
CPC ........ *A61N 1/36046* (2013.01); *A61F 9/0017* (2013.01); *A61N 1/0543* (2013.01); *A61N 1/37205* (2013.01)

(58) Field of Classification Search
None
See application file for complete search history.

(56) References Cited

U.S. PATENT DOCUMENTS

| | | |
|---|---|---|
| 5,597,381 A | 1/1997 | Rizzo, III |
| 6,368,349 B1 | 4/2002 | Wyatt et al. |
| 8,150,526 B2 | 4/2012 | Gross |
| 8,428,740 B2 | 4/2013 | Gefen |
| 8,442,641 B2 | 5/2013 | Gross |
| 8,571,669 B2 | 10/2013 | Liran et al. |
| 8,706,243 B2 | 4/2014 | Gefen et al. |
| 8,718,784 B2 | 5/2014 | Gefen et al. |

(Continued)

FOREIGN PATENT DOCUMENTS

| | | |
|---|---|---|
| WO | 02/091934 | 11/2002 |
| WO | 2010/089739 | 8/2010 |

(Continued)

OTHER PUBLICATIONS

An International Search Report and a Written Opinion both dated Jul. 8, 2019, which issued during the prosecution of Applicant's PCT/IL2019/050484.

(Continued)

*Primary Examiner* — Brian T Gedeon
(74) *Attorney, Agent, or Firm* — Sughrue Mion, PLLC

(57) ABSTRACT

Apparatus is provided that includes an array of stimulating electrodes configured for implantation in a retina of a subject's eye; circuitry configured to drive the electrodes to apply currents to the retina; and a graspable portion coupled to the array and configured to facilitate positioning of the array in an epi-retinal position. A cord is removably coupled to the apparatus and (a) is not electrically coupled to the circuitry, and (b) is looped through an opening of the graspable portion. Other embodiments are also described.

20 Claims, 11 Drawing Sheets

(56) References Cited

U.S. PATENT DOCUMENTS

| | | | |
|---|---|---|---|
| 9,192,464 B2 | 11/2015 | Liran et al. |
| 9,192,772 B1 | 11/2015 | Tsukamoto et al. |
| 9,198,753 B2 | 12/2015 | Gefen et al. |
| 9,265,945 B2 | 2/2016 | Gross et al. |
| 9,331,791 B2 | 5/2016 | Liran et al. |
| 9,370,417 B2 | 6/2016 | Gefen |
| 9,474,902 B2 | 10/2016 | Gefen et al. |
| 9,566,191 B2 | 2/2017 | Gefen et al. |
| 10,226,625 B2 | 3/2019 | Weinberger et al. |
| 2003/0014089 A1 | 1/2003 | Chow et al. |
| 2004/0039401 A1 | 2/2004 | Chow et al. |
| 2004/0054407 A1 | 3/2004 | Tashiro et al. |
| 2004/0078064 A1 | 4/2004 | Suzuki |
| 2005/0165409 A1 | 7/2005 | Eckmiller |
| 2006/0116743 A1 | 6/2006 | Gibson et al. |
| 2006/0224212 A1 | 10/2006 | Kennedy |
| 2008/0288067 A1 | 11/2008 | Flood |
| 2009/0216295 A1 | 8/2009 | Zrenner et al. |
| 2010/0121444 A1 | 5/2010 | Ben Nun |
| 2011/0313522 A1 | 12/2011 | Hayes |
| 2012/0065704 A1 | 3/2012 | Kavasssery et al. |
| 2012/0239126 A1 | 9/2012 | Zhou et al. |
| 2012/0259410 A1 | 10/2012 | Gefen et al. |
| 2014/0046418 A1 | 2/2014 | Williams et al. |
| 2014/0143559 A1 | 5/2014 | Gefen et al. |
| 2015/0342723 A1 | 12/2015 | Abramson et al. |
| 2016/0099046 A1 | 4/2016 | Liran |
| 2016/0105968 A1 | 4/2016 | Tai et al. |
| 2016/0220828 A1 | 8/2016 | Yan Poon et al. |
| 2017/0368351 A1 | 12/2017 | Liran |
| 2018/0117329 A1 | 5/2018 | Degtiar et al. |
| 2018/0117330 A1 | 5/2018 | Weinberger et al. |

FOREIGN PATENT DOCUMENTS

| | | |
|---|---|---|
| WO | 2011/086545 | 7/2011 |
| WO | 2012/017426 | 2/2012 |
| WO | 2012/114327 | 8/2012 |
| WO | 2012/153325 | 11/2012 |
| WO | 2014/080343 | 5/2014 |
| WO | 2014/141089 | 9/2014 |
| WO | 2015/101932 | 7/2015 |
| WO | 2015/110933 | 7/2015 |

OTHER PUBLICATIONS

Roessler, G., Laube, T., Brockmann, C., Kirschkamp, T., Mazinani, B., Menzel-Severing, J., Bornfeld, N., Walter, P. and EPIRET Group, 2011. Angiographic findings following tack fixation of a wireless epiretinal retina implant device in blind RP patients. Graefe's Archive for Clinical and Experimental Ophthalmology, 249(9), pp. 1281-1286.

Ivastinovic, D., Langmann, G., Asslaber, M., Georgi, T., Wedrich, A. and Velikay-Parel, M., 2012. Distribution of glial fibrillary acidic protein accumulation after retinal tack insertion for intraocular fixation of epiretinal implants. Acta ophthalmologica, 90(5), pp. c416-c417.

Laube, T., Brockmann, C., Roessler, G., Walter, P., Krueger, C., Goertz, M., Klauke, S. and Bornfeld, N., 2012. Development of surgical techniques for implantation of a wireless intraocular epiretinal retina implant in Göttingen minipigs. Graefe's Archive for Clinical and Experimental Ophthalmology, 250(1), pp. 51-59.

Menzel-Severing, J., Sellhaus, B., Laube, T., Brockmann, C., Bornfeld, N., Walter, P. and Roessler, G., 2011. Surgical results and microscopic analysis of the tissue reaction following implantation and explantation of an intraocular implant for epiretinal stimulation in minipigs. Ophthalmic research, 46(4), pp. 192-198.

Gekeler, F., Szurman, P., Grisanti, S., Weiler, U., Claus, R., Greiner, T.O., Völker, M., Kohler, K., Zrenner, E. and Bartz-Schmidt, K.U., 2007. Compound subretinal prostheses with extra-ocular parts designed for human trials: successful long-term implantation in pigs. Graefe's Archive for Clinical and Experimental Ophthalmology, 245(2), pp. 230-241.

An Office Action dated Apr. 27, 2018, which issued during the prosecution of U.S. Appl. No. 15/342,765.

An Office Action dated Jan. 11, 2018, which issued during the prosecution of U.S. Appl. No. 15/342,765.

Yang et al. Surgical results of pars plana vitrectomy combined with phacoemulsification J Zhejian Univ Science B 20067(2):129-132.

An Office Action dated Sep. 22, 2017, which issued during the prosecution of U.S. Appl. No. 15/195,212.

Pham et al. Self Closing corneosceleral tunnel incision in cataract surgery, Opthalmaloge. Feb. 1996;93(1):8-1 1.

An Office Action dated Feb. 23, 2018, which issued during the prosecution of U.S. Appl. No. 15/195,212.

An Invitation to pay additional fees dated Feb. 16, 2018, which issued during the prosecution of Applicant's PCT/IL2017/051202.

Notice of Allowance dated Oct. 29, 2018, which issued during the prosecution of U.S. Appl. No. 15/342,765.

Notice of Allowance dated Feb. 27, 2019, which issued during the prosecution of U.S. Appl. No. 15/342,746.

Notice of Allowance dated Feb. 6, 2019, which issued during the prosecution of U.S. Appl. No. 15/342,746.

An Office Action dated May 16, 2018, which issued during the prosecution of U.S. Appl. No. 15/342,746.

An International Search Report and a Written Opinion both dated May 4, 2018, which issued during the prosecution of Applicant's PCT/IL2017/051202.

An Office Action dated Dec. 11, 2018, which issued during the prosecution of U.S. Appl. No. 15/342,746.

An Office Action dated Feb. 21, 2018, which issued during the prosecution of U.S. Appl. No. 15/342,746.

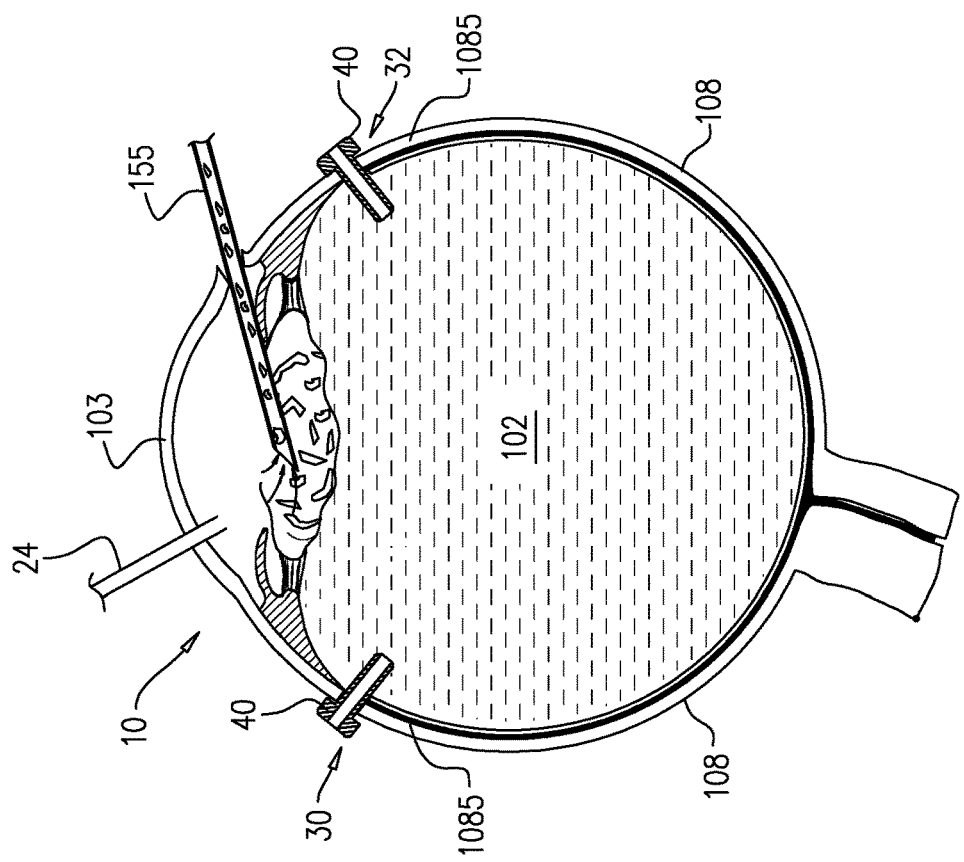
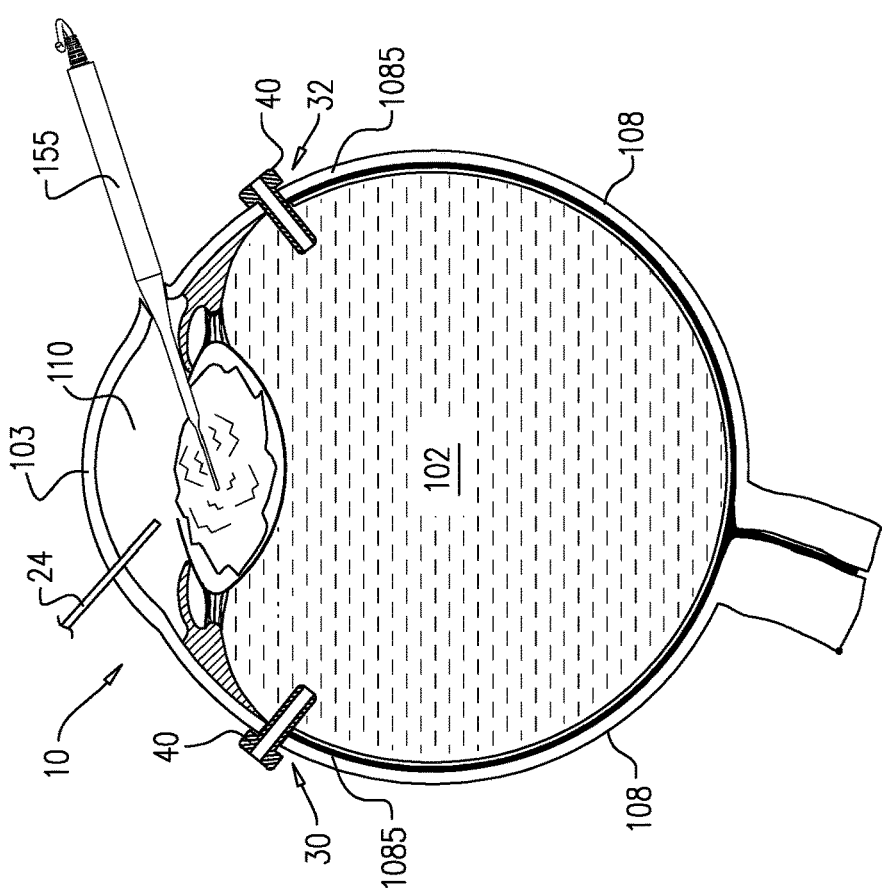
FIG. 4A
FIG. 4B

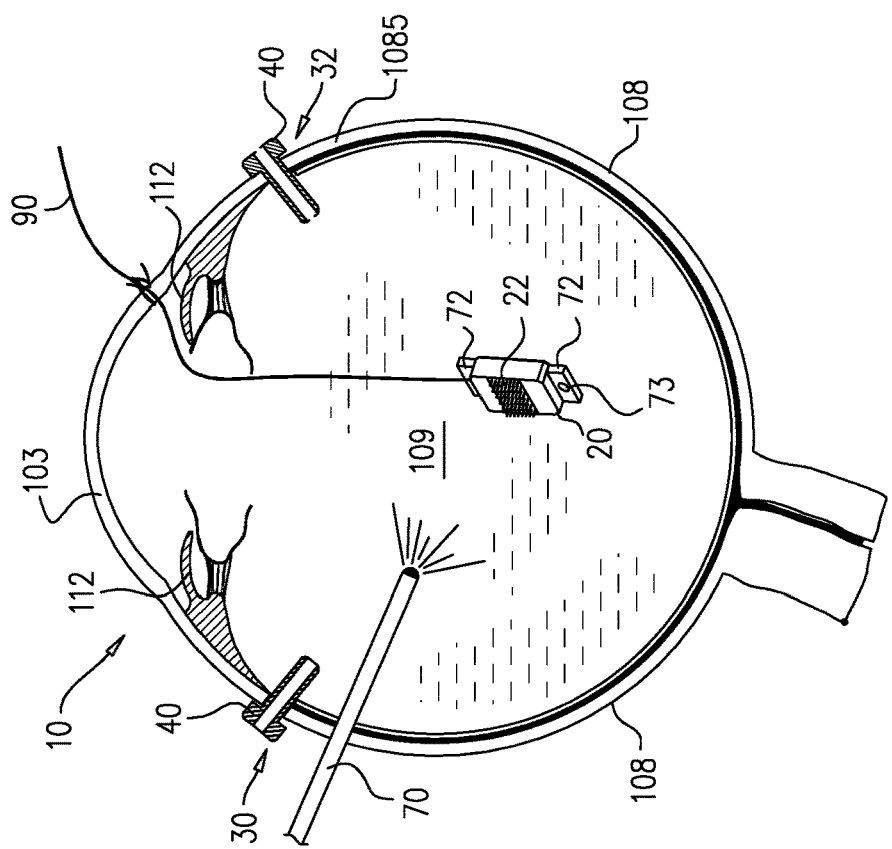
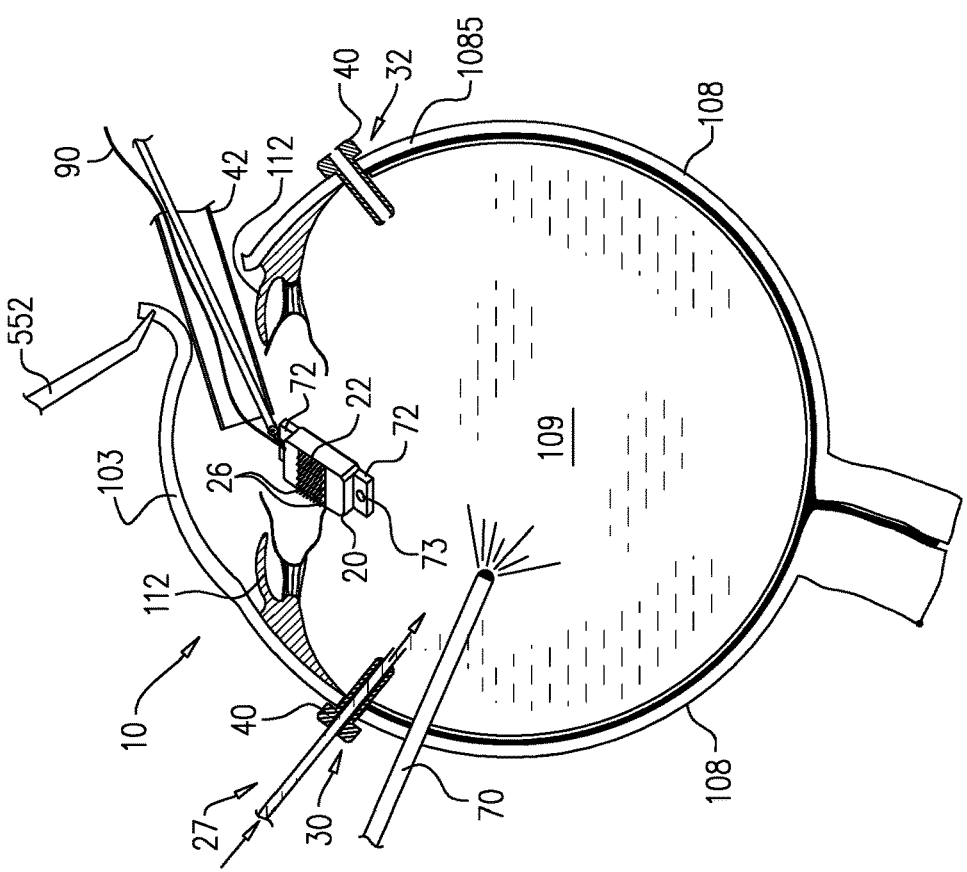
FIG. 8A
FIG. 8B

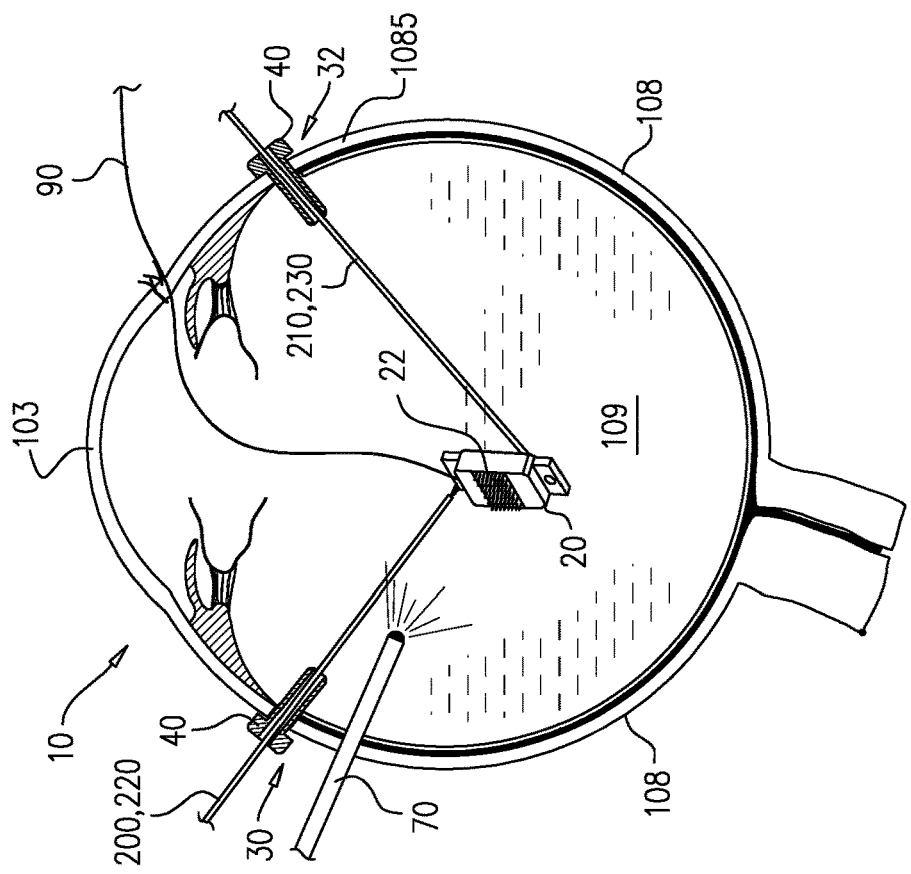
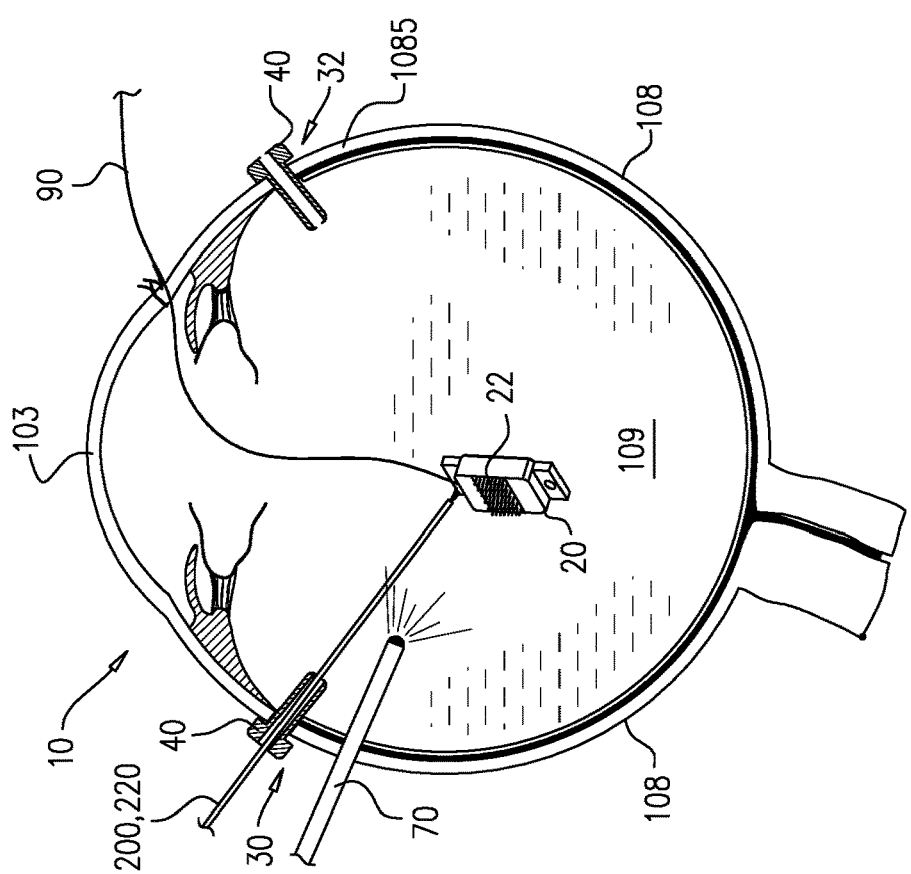

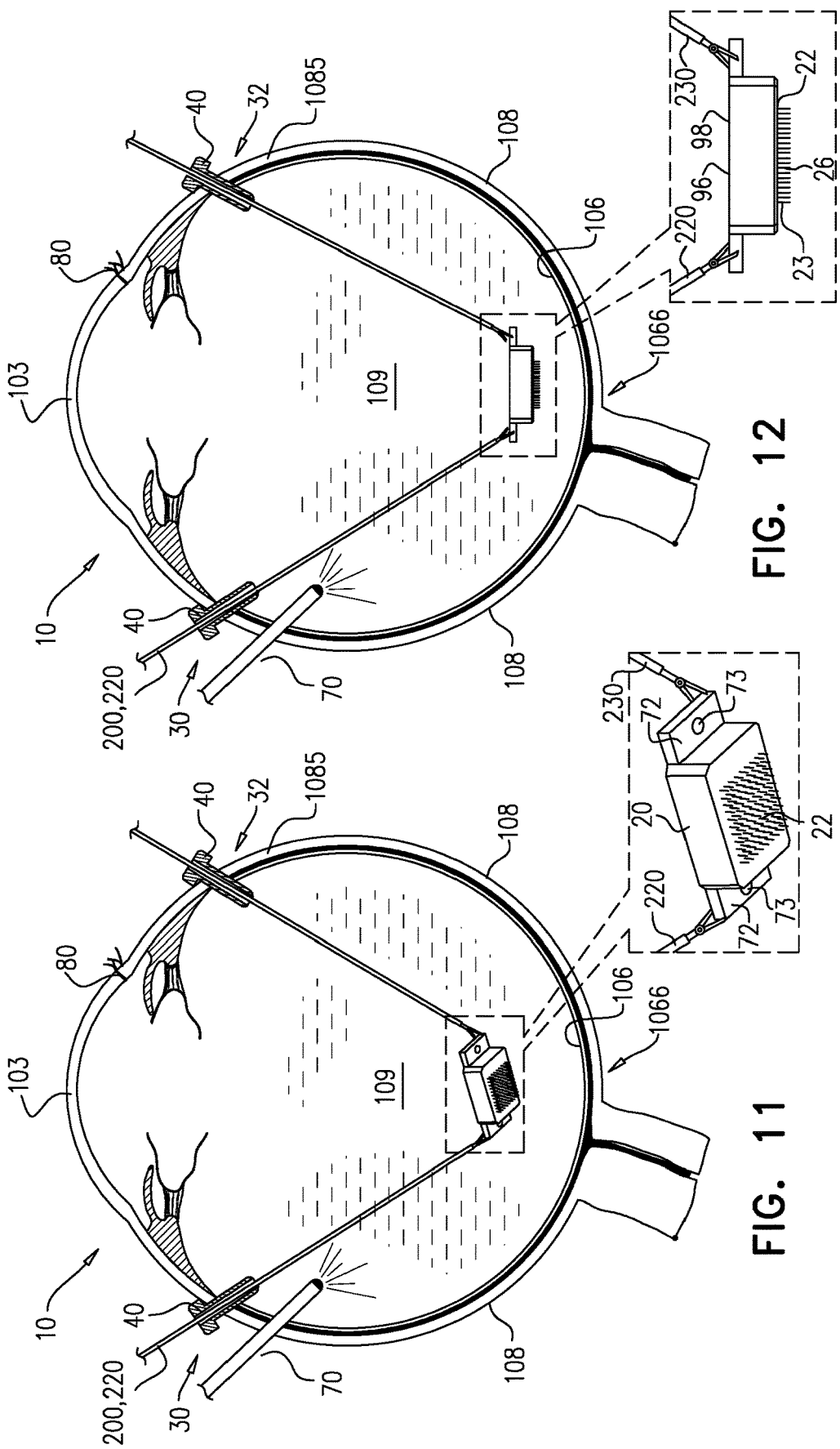

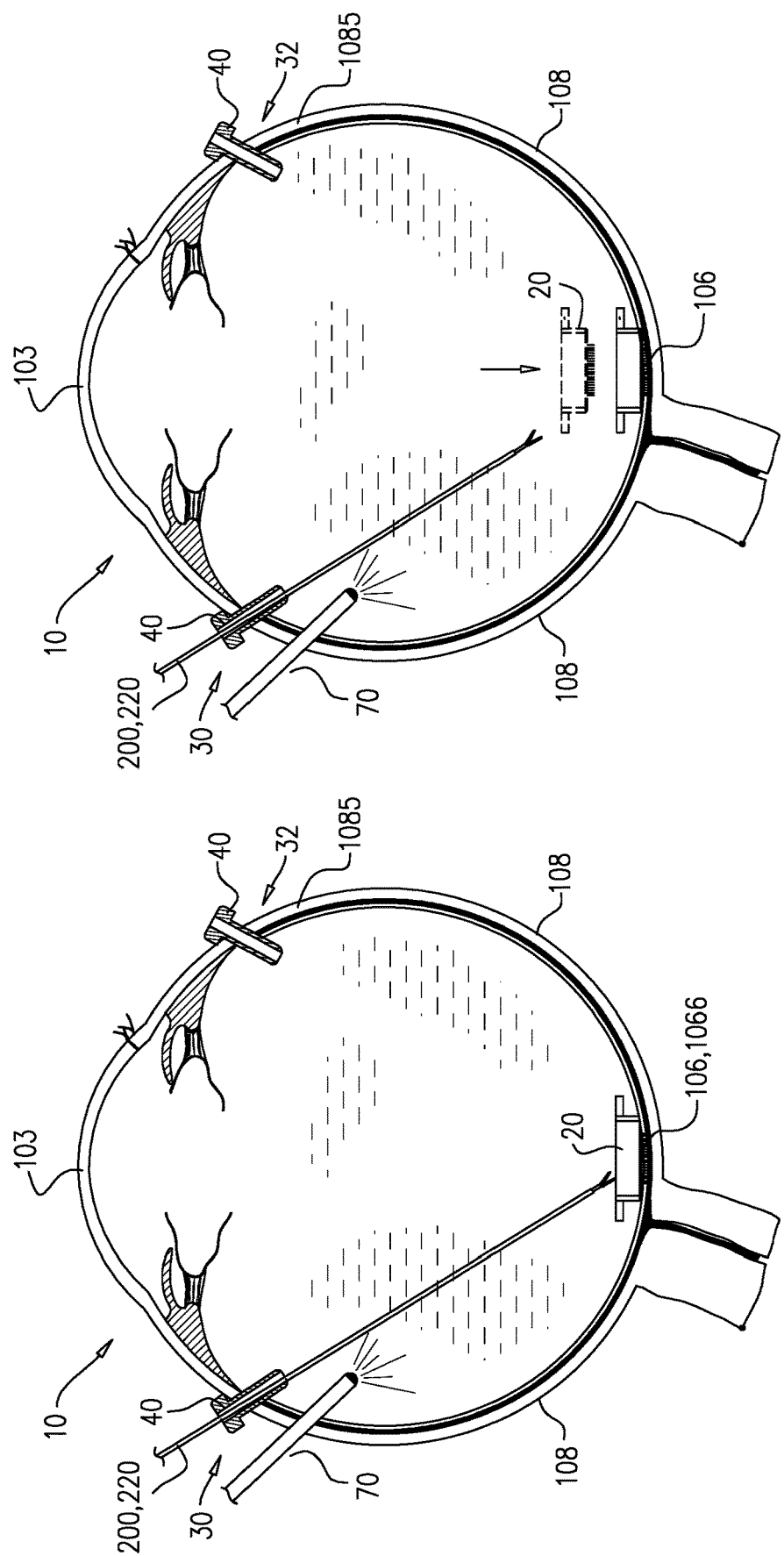

RETINAL IMPLANT WITH INSERTION CORD

CROSS-REFERENCE TO RELATED APPLICATIONS

The present application is a continuation of U.S. application Ser. No. 15/342,765, filed Nov. 3, 2016, which is related to U.S. application Ser. No. 15/342,746 to Degtiar et al., filed Nov. 3, 2016, entitled, "Retinal Implant Fixation," which is assigned to the assignee of the present application and is incorporated herein by reference.

FIELD OF THE INVENTION

The present invention relates generally to implantable medical devices, and specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retina-related blindness.

The retina is a multi-layered light-sensitive structure that lines the posterior, inner part of the eye. The retina contains photoreceptor cells, rods and cones, which capture light and convert light signals into neural signals transmitted through the optic nerve to the brain. Rods are responsible for light sensitive, low resolution black and white vision, whereas cones are responsible for sharp, high resolution color vision.

SUMMARY OF THE INVENTION

In accordance with some applications of the present invention, a method is provided for implanting apparatus on a retina of the subject. Typically, the apparatus comprises an implantable retinal simulator configured to stimulate the retina of the subject suffering from a retinal disease in order to restore at least partial vision in the subject. Typically, the apparatus comprises an electrode array comprising electrodes for stimulation of the retina which are shaped to define distal tips protruding from the array, a plurality of photosensors, and driving circuitry configured to drive the electrodes to apply currents to the retina in response to signals from the photosensors. The apparatus is typically implanted in an epi-retinal position, and the electrode array typically penetrates the retina. In accordance with some applications of the present invention, surgical techniques are provided for introducing the apparatus into the eye and for placing the apparatus on the retina.

For some applications, the method comprises removing a lens and a vitreous body of the eye and inserting the apparatus through a corneoscleral incision into a vitreous cavity of the subject's eye. During inserting of the apparatus, an orientation of the distal tips of the electrodes is maintained pointing towards a cornea of the eye. Typically, maintaining the orientation of the distal tips pointing towards the cornea allows identifying possible damage to the distal tips that may have occurred during the inserting and in such cases the apparatus is removed from the eye without being implanted.

Subsequently to inserting the apparatus into the eye through the corneoscleral incision, the apparatus is rotated such that the distal tips of the electrodes point towards a macula of the eye. Typically, the apparatus is rotated by one or more tools, e.g., first and second grasping tools, which grasp the apparatus and rotate it. Typically, the one or more tools are inserted into the vitreous cavity through at least one opening, e.g., two openings, in a posterior-segment scleral wall of the eye.

Subsequently to the rotating, the apparatus is positioned on the retina in an epi-retinal position, such that the distal tips of the electrodes penetrate the retina. For some applications, the apparatus is positioned on the retina using the first and second grasping tools. Alternatively, the apparatus is positioned on the retina using one grasping tool to grasp the apparatus and using a non-grasping tool to apply the apparatus to the retina while not grasping the apparatus by the non-grasping tool. For some applications, prior to positioning the apparatus onto the retina, the apparatus is dropped onto the retina typically from a height of 0.5-1.5 mm above the retina.

There is therefore provided in accordance with some applications of the present invention, a method for implanting, in an eye of a subject apparatus configured for implantation on a retina of the subject, and having (i) an electrode array including a plurality of stimulating electrodes shaped to define distal tips protruding from the array (ii) a plurality of photosensors; and (iii) driving circuitry, configured to drive the electrodes to apply currents to the retina, the method including:

removing a lens of the eye and a vitreous body of the eye;

creating a corneoscleral incision and inserting the apparatus through the corneoscleral incision into a vitreous cavity of the subject's eye;

during the inserting, maintaining an orientation of the distal tips pointing towards a cornea of the eye;

subsequently to the inserting, rotating the apparatus such that the distal tips point towards a macula of the eye;

subsequently to the rotating, positioning the apparatus in an epi-retinal position such that the distal tips of the electrodes penetrate the retina.

For some applications, the method further includes prior to the positioning the apparatus, dropping the apparatus onto the retina.

For some applications dropping includes dropping the apparatus from 0.5-1.5 mm above the retina.

For some applications, the method further includes subsequently to the inserting, grasping the apparatus by first and second grasping tools, and:

rotating the apparatus includes rotating the apparatus using the first and second grasping tools; and positioning the apparatus in an epi-retinal position includes positioning the apparatus using at least one of the first and the second grasping tools.

For some applications, positioning the apparatus using at least one of the first and the second grasping tools includes positioning the apparatus using only one of the grasping tools.

For some applications, the method further includes inserting the first grasping tool into the vitreous cavity through a first opening in a posterior-segment scleral wall, and grasping by the first grasping tool includes grasping by the first grasping tool after insertion of the first grasping tool through the first opening in the posterior-segment scleral wall; and inserting the second grasping tool into the vitreous cavity through a second opening in the posterior-segment scleral wall, and grasping by the second grasping tool includes grasping by the second grasping tool after insertion of the second grasping tool through the second opening in the posterior-segment scleral wall.

For some applications, the method further includes providing a cord removably coupled to the apparatus; and inserting includes inserting the apparatus into the vitreous cavity while the cord is removably coupled to the apparatus and at least one end of the cord is disposed outside the subject's eye during the inserting;

the method further including:

removing the cord from the subject's eye, subsequently to the grasping of the apparatus by the first grasping tool, and prior to the positioning of the apparatus in the epi-retinal position.

For some applications, the method further includes subsequently to the inserting, grasping the apparatus by one or more grasping tools, and:

rotating the apparatus includes rotating the apparatus using the one or more grasping tools; and positioning the apparatus in an epi-retinal position includes positioning the apparatus using at least one grasping tool.

For some applications, positioning the apparatus using at least one grasping tool includes positioning the apparatus using exactly one grasping tool.

For some applications, rotating the apparatus using the one or more grasping tools includes rotating the apparatus using exactly one grasping tool.

For some applications, the method further includes subsequently to the inserting, advancing into the vitreous cavity one or more tools, and:

rotating the apparatus includes rotating the apparatus using the one or more tools; and positioning the apparatus in an epi-retinal position includes positioning the apparatus using the one or more tools.

For some applications, the one or more tools include at least one grasping tool and at least one non-grasping tool and rotating the apparatus includes rotating the apparatus using at least one of: the at least one grasping tool and the at least one non-grasping tool.

For some applications, the one or more tools include at least one grasping tool and at least one non-grasping tool, and positioning the apparatus includes positioning the apparatus using at least one of the at least one grasping tool to grasp the apparatus and at least one of the at least one non-grasping tools to apply the apparatus to the retina while not grasping the apparatus by the non-grasping tool.

There is further provided in accordance with some applications of the present invention, a method for implanting, in an eye of a subject, apparatus configured for implantation on a retina of the subject, and having (i) an electrode array including a plurality of stimulating electrodes shaped to define distal tips protruding from the array (ii) a plurality of photosensors; and (iii) driving circuitry, configured to drive the electrodes to apply currents to the retina, the method including:

removing a lens of the eye and a vitreous body of the eye;

creating a corneoscleral incision and inserting the apparatus through the corneoscleral incision into a vitreous cavity of the subject's eye;

during the inserting, maintaining an orientation of the distal tips pointing towards a cornea of the eye;

subsequently to the inserting, rotating the apparatus such that the distal tips point towards a macula of the eye;

subsequently to the rotating, dropping the apparatus onto the retina such that the apparatus is positioned on the retina in an epi-retinal position and the distal tips of the electrodes penetrate the retina.

For some applications, dropping includes dropping the apparatus onto the retina from 0.5-1.5 mm above the retina.

For some applications, the apparatus has a density of 1.5-2 g/cc, and dropping the apparatus includes dropping the apparatus having the density of 1.5-2 g/cc.

For some applications, the method further includes subsequently to the inserting, grasping the apparatus by first and second grasping tools, and:

rotating the apparatus includes rotating the apparatus using the first and second grasping tools.

There is further provided in accordance with some applications of the present invention, a method for implanting, in an eye of a subject, apparatus configured for implantation on a retina of the subject, and having (i) an electrode array including a plurality of stimulating electrodes shaped to define distal tips protruding from the array (ii) a plurality of photosensors; and (iii) driving circuitry, configured to drive the electrodes to apply currents to the retina, the method including:

creating a corneoscleral incision and inserting the apparatus through the corneoscleral incision into a vitreous cavity of the subject's eye;

during the inserting, maintaining an orientation of the distal tips pointing towards a cornea of the eye;

identifying damage to the distal tips that occurred during the inserting; and in response to identifying the damage, removing the apparatus through the corneoscleral incision without implanting the apparatus.

There is further provided in accordance with some applications of the present invention, a method for implanting in an eye of a subject, apparatus configured for implantation on a retina of the subject, and having (i) an electrode array including a plurality of stimulating electrodes shaped to define distal tips protruding from the array (ii) a plurality of photosensors; and (iii) driving circuitry, configured to drive the electrodes to apply currents to the retina, the method including:

removing a lens of the eye and a vitreous body of the eye;

creating a corneoscleral incision and inserting the apparatus through the corneoscleral incision into a vitreous cavity of the subject's eye;

subsequently to the inserting, grasping the apparatus by a first grasping tool;

using the first grasping tool, rotating the apparatus such that the distal tips point towards a macula of the eye;

subsequently to the rotating, using the first grasping tool, positioning the apparatus in an epi-retinal position such that the distal tips of the electrodes penetrate the retina.

For some applications, the method further includes suturing the corneoscleral incision subsequently to the inserting and prior to the grasping of the apparatus.

For some applications, the method further includes grasping the apparatus by a second grasping tool, and rotating the apparatus includes rotating the apparatus using the first and second grasping tools.

For some applications, positioning the apparatus using the first and second grasping tools includes:

using one of the grasping tools to grasp the apparatus; and using the other one of the grasping tools to apply the apparatus to the retina while the other one of the grasping tools is not grasping the apparatus.

For some applications, the method further includes prior to the positioning the apparatus, dropping the apparatus onto the retina.

For some applications, the method further includes providing a cord removably coupled to the apparatus, and inserting includes inserting the apparatus into the vitreous cavity while the cord is removably coupled to the apparatus and at least one end of the cord is disposed outside the subject's eye during the inserting, the method further including removing the cord from the subject's eye, subsequently to the grasping of the apparatus by the first grasping tool, and prior to the positioning of the apparatus in the epi-retinal position.

For some applications, the method further includes:

subsequently to inserting the apparatus, inhibiting advancement of the cord into the eye by tying the cord outside the eye; and untying the cord prior to the positioning of the apparatus in the epi-retinal position.

There is further provided in accordance with some applications of the present invention, apparatus including:

an array of stimulating electrodes configured for implantation in a retina of a subject's eye;

circuitry configured to drive the electrodes to apply currents to the retina;

a graspable portion coupled to the array and configured to facilitate positioning of the array in an epi-retinal position; and a cord removably coupled to the apparatus and (a) being not electrically coupled to the circuitry, and (b) looped through an opening of the graspable portion.

For some applications, the cord has a length of at least 3 cm.

For some applications, the cord has a length that is less than 20 cm.

For some applications, the cord has a diameter of 20-50 microns.

For some applications, the graspable portion has an area of 1-4 mm^2.

For some applications, the graspable portion includes a wire frame.

For some applications, the cord is looped through the opening of the graspable portion by being tied to the portion of the graspable portion.

The present invention will be more fully understood from the following detailed description of applications thereof, taken together with the drawings, in which:

BRIEF DESCRIPTION OF THE DRAWINGS

FIGS. 4A-B are schematic illustrations of a cross section of the eye showing removal of a lens of the subject through the corneoscleral incision, in accordance with some applications of the present invention;

FIGS. 8A-B are schematic illustrations of a cross section of the eye showing the insertion of the apparatus into the eye, in accordance with some applications of the present invention;

FIG. 9 is a schematic illustration of a cross section of the eye showing a first tool inserted into the eye and engaging the apparatus, in accordance with some applications of the present invention;

FIG. 10 is a schematic illustration of a cross section of the eye showing a second tool inserted into the eye and engaging the apparatus, in accordance with some applications of the present invention;

FIG. 11 is a schematic illustration of a cross section of the eye showing the first and second tools rotating the apparatus, in accordance with some applications of the present invention;

FIG. 12 is a schematic illustration of a cross section of the eye showing the apparatus positioned on the retina of the subject, in accordance with some applications of the present invention;

FIG. 13 is a schematic illustration of a cross section of the eye showing the apparatus being pressed against the retina of the subject, in order to cause electrodes of the apparatus to penetrate the retina, in accordance with some applications of the present invention;

FIG. 14 is a schematic illustration of a cross section of the eye showing the apparatus dropped onto the retina of the subject, in accordance with some applications of the present invention;

DETAILED DESCRIPTION OF EMBODIMENTS

FIGS. 1-18 are schematic illustrations of the surgical procedure for implantation of apparatus 20 for stimulation of a retina 106, in accordance with some applications of the present invention. In particular, FIGS. 1-18 describe introducing apparatus 20 into eye 10 and positioning the apparatus on retina 106.

Figure 1:
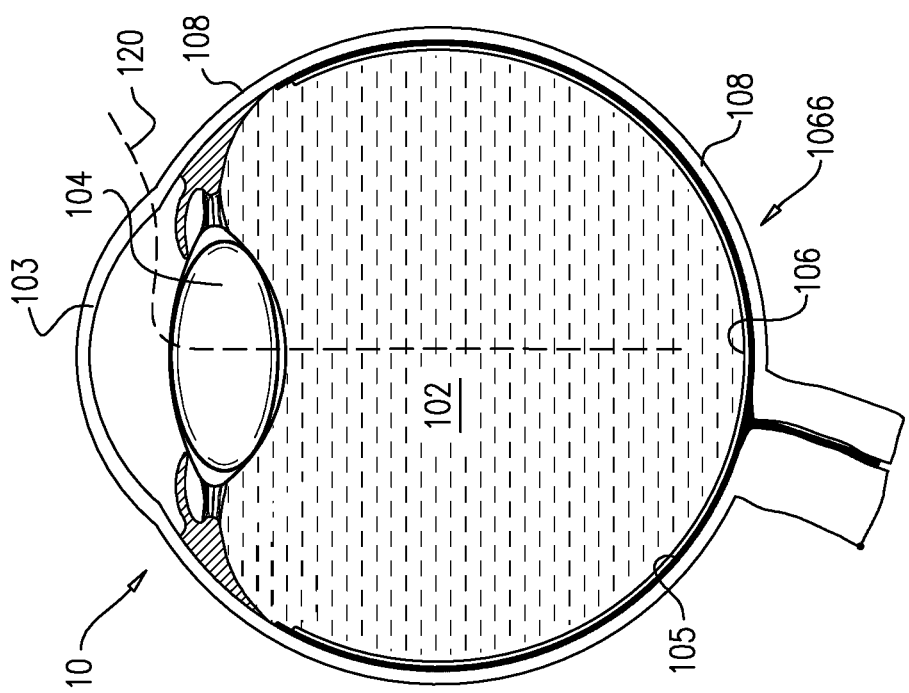
FIG. 1 is a schematic illustration of a cross section of an eye of a subject showing a path by which apparatus is to be implanted in accordance with some applications of the present invention.
Figure 3:
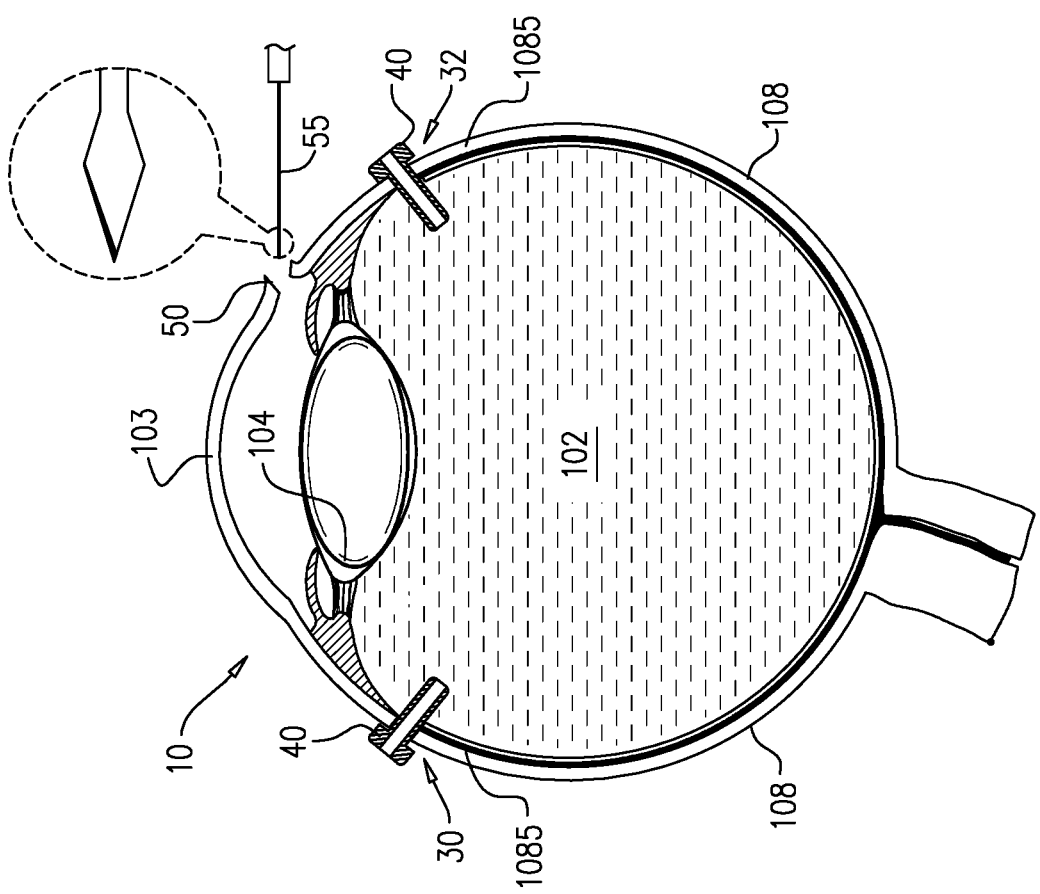
FIG. 3 is a schematic illustration of a cross section of the eye showing a corneoscleral incision created in the eye for insertion of the apparatus therethrough, in accordance with some applications of the present invention.

Reference is first made to FIG. 1, which is a schematic illustration of a cross section of eye 10 of the subject showing a path 120 by which apparatus 20 is to be implanted in eye 10. FIG. 1 additionally shows cornea 103, vitreous body 102, lens 104, sclera 108, choroid 105, retina 106 and macula 1066.

Figure 2:
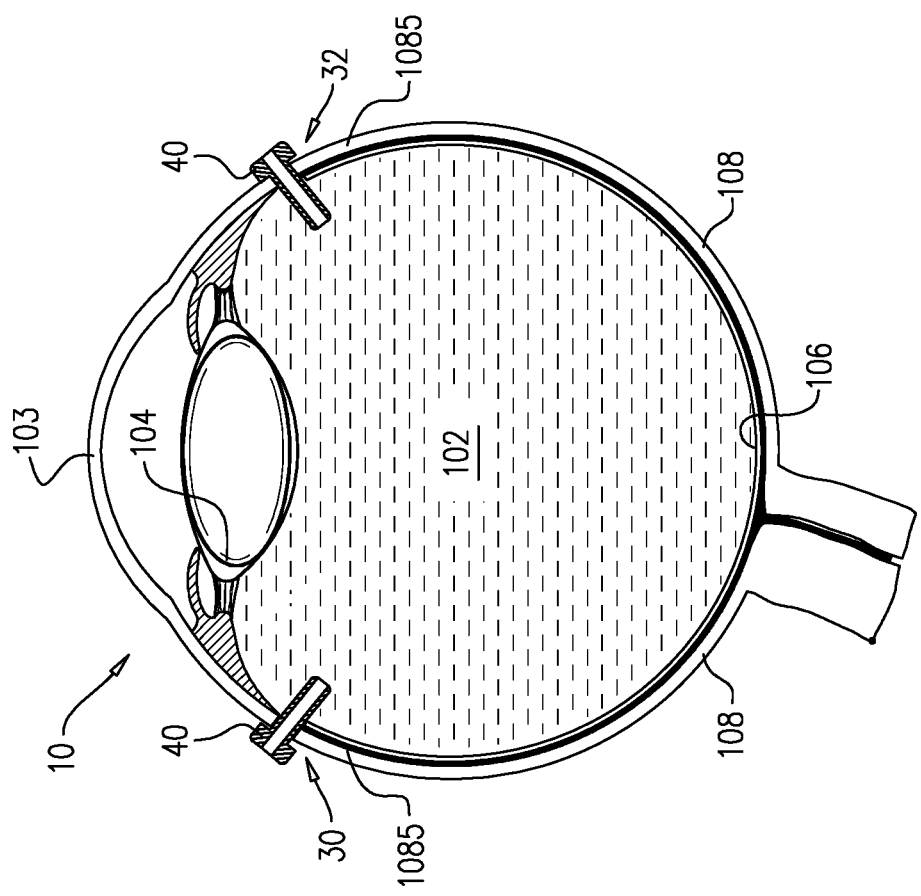
FIG. 2 is a schematic illustration of a cross section of the eye showing openings in a posterior-segment scleral wall of the eye, created for insertion of one or more tools therethrough, in accordance with some applications of the present invention.

Reference is now made to FIG. 2 which is a schematic illustration of a cross section of eye 10 showing openings in a posterior-segment scleral wall 1085 of eye 10, created for insertion of one or more tools therethrough, in accordance with some applications of the present invention. For some applications, in order to facilitate the implantation procedure, at least one opening 30, e.g., a first opening 30 and a second opening 32 (on each side of eye 10, as shown) are created in sclera 108. As shown, openings 30 and 32 are typically created in posterior-segment scleral wall 1085 of eye 10. Openings 30 and 32 are typically created by puncturing posterior-segment scleral wall 1085 with a tool, e.g., with a trocar (not shown). A cannula 40 is then typically advanced over (i.e., around) the trocar, and the trocar is then removed. Cannula 40 is typically positioned in openings 30 and 32 to function as a port for the subsequent placement in eye 10 of other instruments, such as graspers and/or other tools, as described hereinbelow.

Figure 5:
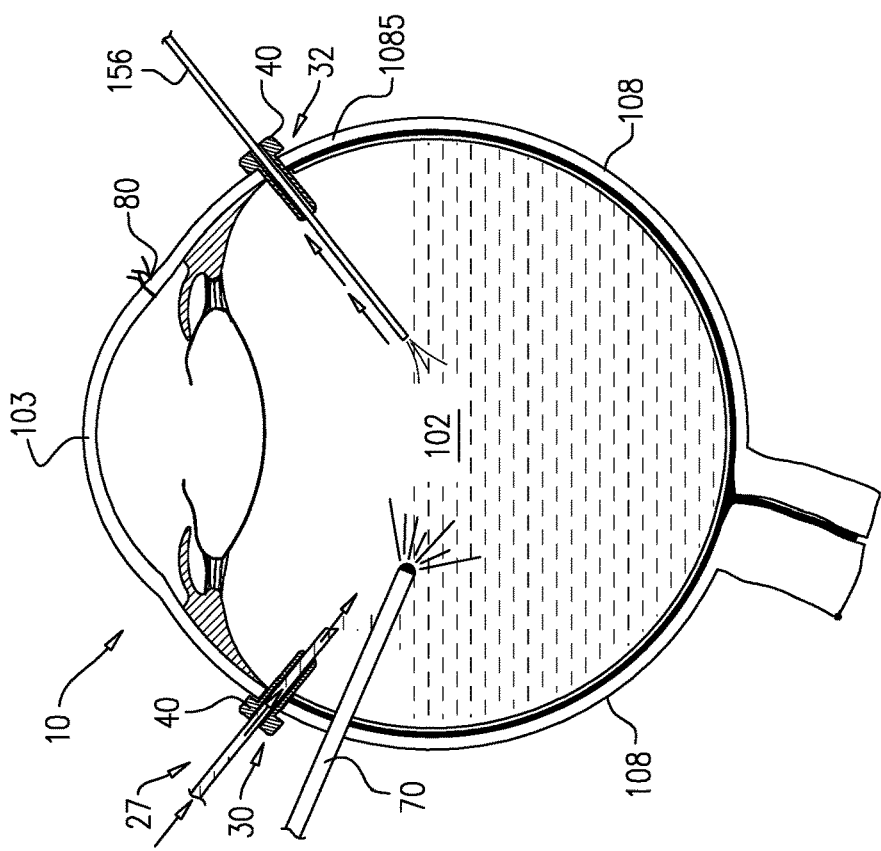
FIG. 5 is a schematic illustration of a cross section of the eye showing removal of a vitreous body of the eye through the opening in the posterior-segment scleral wall of the eye and insertion of a fluid into the eye, in accordance with some applications of the present invention.

Reference is now made to FIGS. 3-6. A corneoscleral incision 50 is created in eye 10 (FIG. 3), using a tool 55. Typically, tool 55 comprises a scalpel and/or one or more ocular knives that are used to create corneoscleral incision 50. Subsequently, lens 104 is removed through corneoscleral incision 50 typically using a phacoemulsifier 155 (FIG. 4A-B). Typically, during phacoemulsification of lens 104 (and in some cases, throughout additional steps in the implantation procedure of apparatus 20), an anterior chamber maintainer 24 is positioned in anterior chamber 110. Optionally but not necessarily, following removal of lens 104, corneoscleral incision 50 is temporarily closed with sutures 80, in order to maintain pressure within eye 10 during removal of vitreous body 102 through opening 30 or 32 using a vitrector 156 (FIG. 5). Typically, lens 104 and vitreous body 102 are removed from eye 10 in order to allow subsequent insertion of apparatus 20 into the eye and implantation of apparatus 20 on retina 106. During and following removal of vitreous body 102 and typically throughout implantation of apparatus 20, the posterior segment of the eye is continuously perfused by a fluid 107, for example, a gas or a physiological irrigation solution, e.g., balanced salt solution (BSS). Fluid 107 is typically passed into the eye through a tool, e.g., a posterior maintainer 27, which is inserted through cannula 40 as shown in FIG. 5. The arrows shown in posterior maintainer 27 indicate the flow of fluid 107 into the posterior segment of the eye.

Typically, an illuminator 70 is inserted into eye 10 to provide illumination to the posterior segment of the eye during the vitrectomy and the subsequent implantation procedure of apparatus 20.

Figure 6:
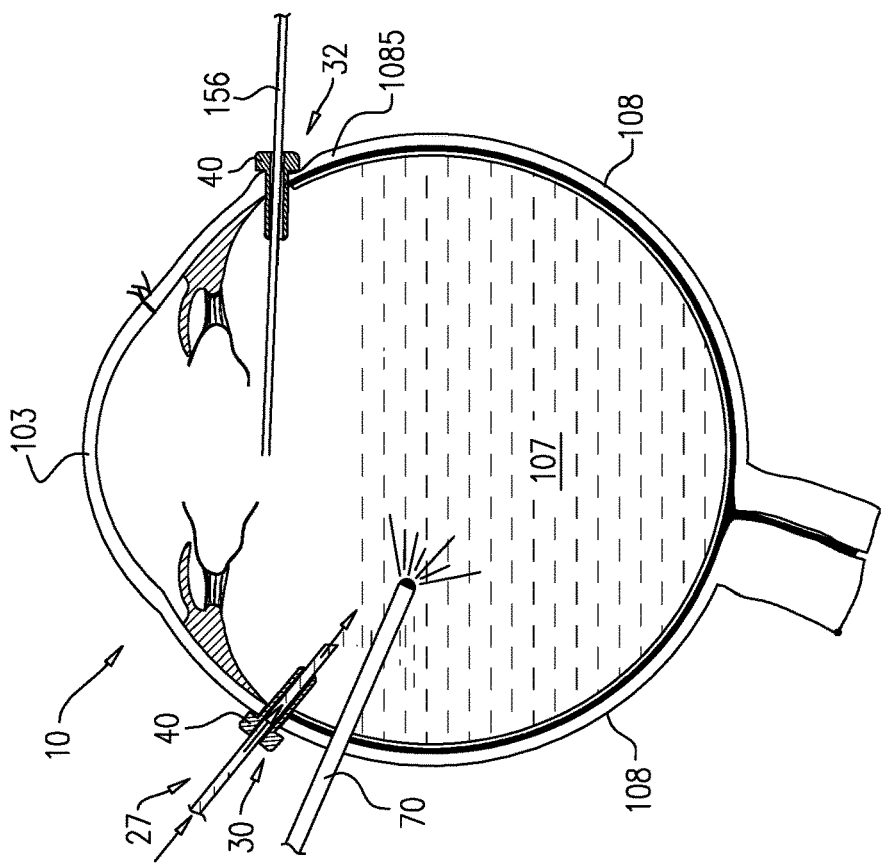
FIG. 6 is a schematic illustration of a cross section of the eye showing cutting of a posterior lens capsule of the subject, in accordance with some applications of the present invention.
Figure 7:
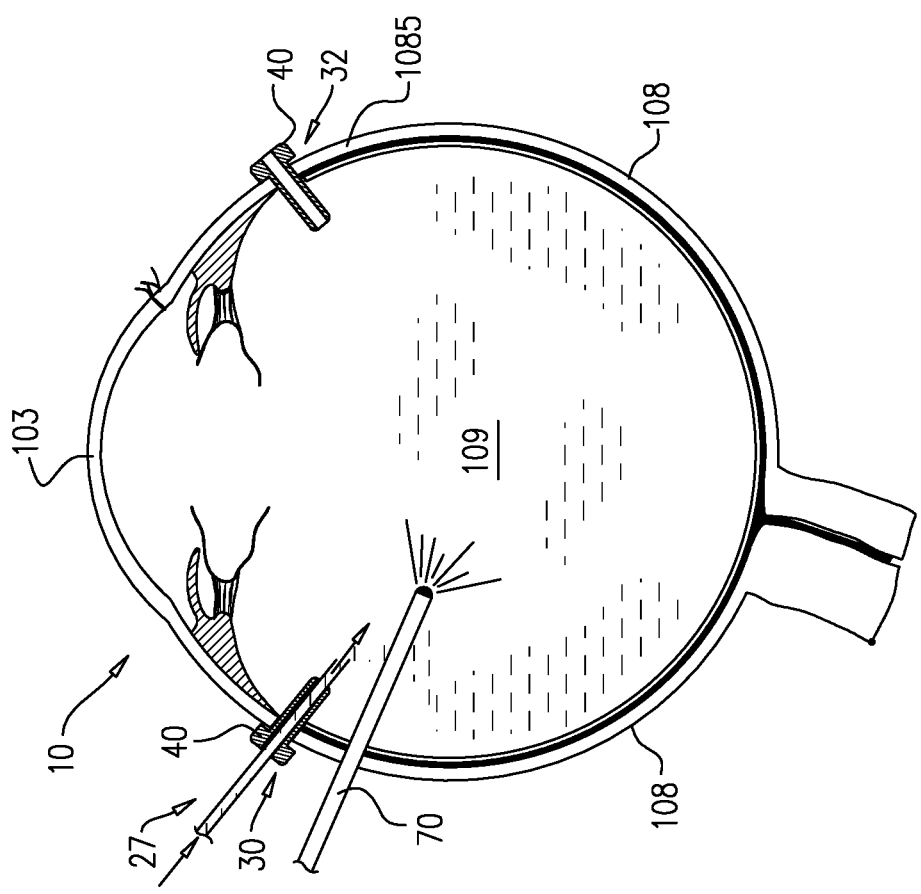
FIG. 7 is a schematic illustration of a cross section of the eye prior to insertion of the apparatus into the eye, in accordance with some applications of the present invention.
Figure 16:
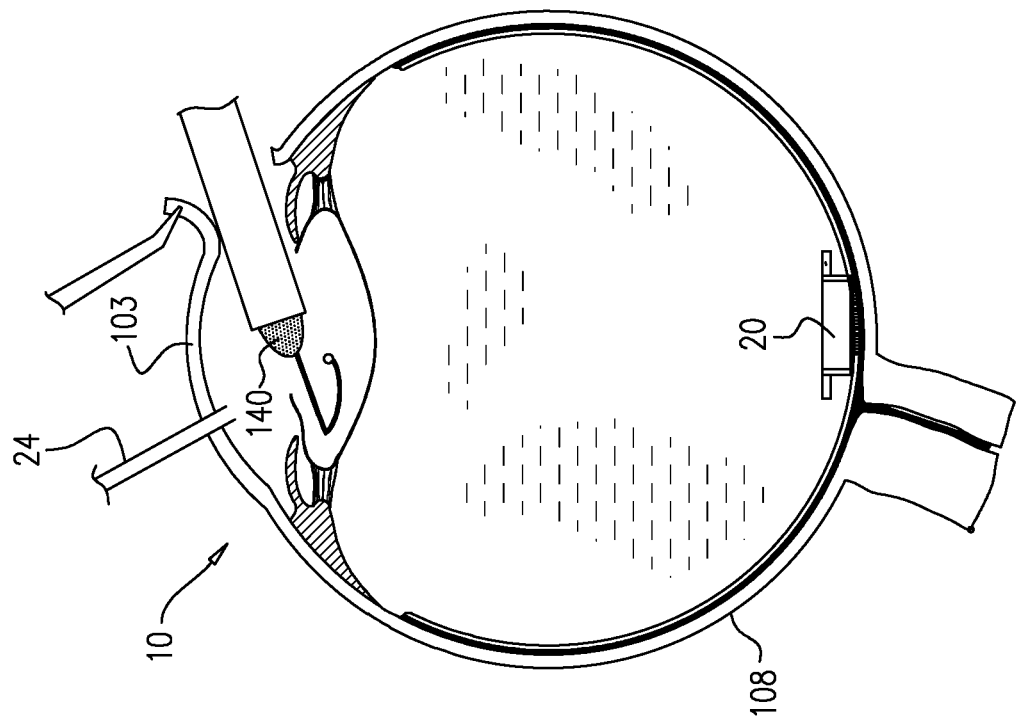
FIGS. 16-17 are schematic illustrations of a cross section of the eye showing an intraocular lens inserted into the eye, in accordance with some applications of the present invention.
Figure 15:
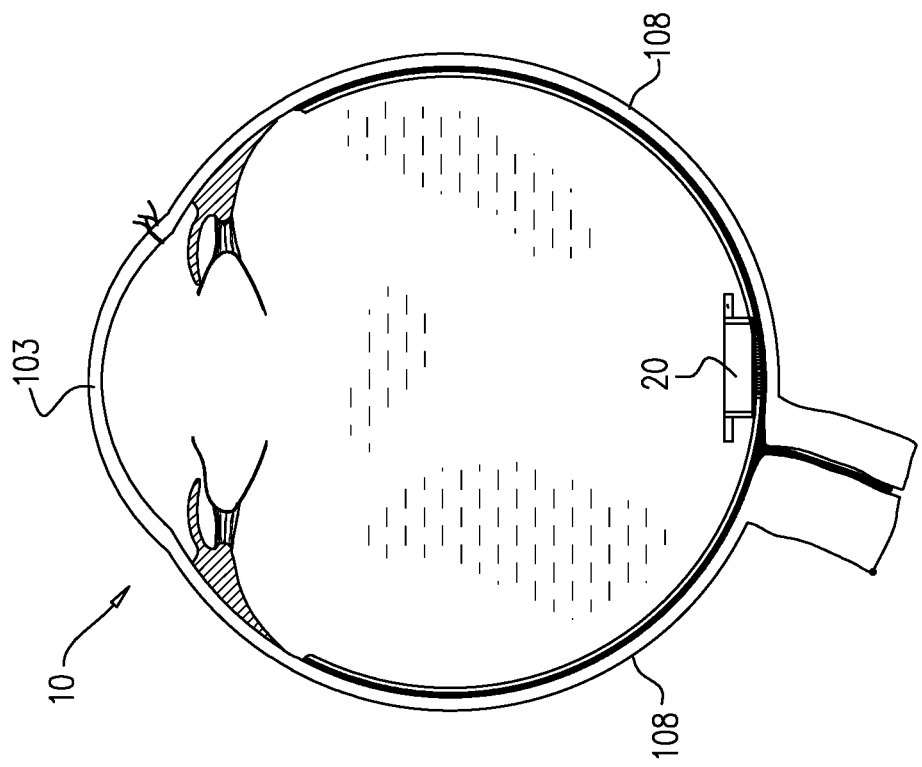
FIG. 15 is a schematic illustration of a cross section of the eye showing the apparatus positioned on the retina of the subject, in accordance with some applications of the present invention.

Reference is now made to FIGS. 6-7. FIG. 6 shows vitrector 156 being used for cutting of a posterior capsule of lens 104 to facilitate subsequent advancement of apparatus 20 into eye 10. As shown, vitrector 156 is typically introduced into eye 10, through opening 30 or 32 in posterior-segment scleral wall 1085. The incision in the posterior capsule of lens 104 is typically, 5-7 mm, e.g., 6 mm long. FIG. 7 is a schematic illustration of cross section of eye 10, prior to insertion of apparatus 20 into eye 10.

Reference is now made to FIGS. 8A-B, which are schematic illustrations of the insertion of apparatus 20 into the eye 10, in accordance with some applications of the present invention. Apparatus 20 typically comprises an electrode array 22 (shown more clearly in FIGS. 11-12) comprising electrodes 23 for stimulation of the retina. Electrodes 23 are each shaped to define distal tips 26 protruding from array 22. Apparatus 20 further comprises a plurality of photosensors 96 and driving circuitry 98 (FIG. 12) configured to drive electrodes 23 to apply currents to the retina in response to signals from photosensors 96.

As shown in FIGS. 8A-B, apparatus 20 is inserted into a vitreous cavity 109 through corneoscleral incision 50. (In cases that sutures 80 were used, sutures 80 are removed from incision 50 in order to allow insertion of apparatus 20 therethrough.) For some applications, incision 50 is increased from about 2-3 mm to about 6-8 mm in length, to facilitate insertion of apparatus 20 therethrough. Optionally, apparatus 20 is introduced into eye 10 through a cannula 42 which is inserted into corneoscleral incision 50. It is noted that apparatus 20 may be introduced into eye 10 without the use of a cannula. For some applications, apparatus 20 is inserted through corneoscleral incision 50 using a grasping tool, e.g., forceps. Apparatus 20 is typically inserted into corneoscleral incision 50 and advanced over iris 112 (iris 112 is typically dilated, as shown) and advanced into vitreous cavity 109 through the pupil of eye 10. A flap of cornea 103 is typically held by forceps 552 while apparatus 20 is being inserted through corneoscleral incision 50.

As shown in FIG. 8A, during inserting (e.g., during the first 5 mm of insertion of apparatus 20 through vitreous cavity 109), apparatus 20 is maintained such that an orientation of distal tips 26 of electrodes 23 points towards cornea 103 of eye 10. Typically, maintaining the orientation of distal tips 26 pointing towards cornea 103 allows identifying possible damage to distal tips 26 that may have occurred during inserting apparatus 20 and in such cases apparatus 20 is removed from eye 10 without being implanted.

As further shown in FIGS. 8A-B, for some applications, a cord 90 is removably coupled to apparatus 20 while apparatus 20 is being advanced into eye 10. During inserting of apparatus 20, cord 90 is tied to, or looped through a portion of apparatus 20 and at least one end of cord 90 is disposed outside eye 10. The end of cord 90 which is disposed outside of eye 10 typically provides control of apparatus 20, e.g., by preventing apparatus 20 from falling onto the retina, without requiring the physician to hold the apparatus in place (e.g., with graspers).

It is noted that cord 90 is not electrically coupled to circuitry 98 of apparatus 20. Cord 90 typically has a length of at least 3 cm and less than 20 cm, and a diameter of 20-50 microns.

For some applications, apparatus 20 further comprises a graspable portion 72, e.g., an edge of the apparatus or a rim of the apparatus. The graspable portion may surround apparatus 20 at least in part. The graspable portion is typically grasped during implantation of apparatus 20 to facilitate positioning of apparatus 20 in an epi-retinal position. Typically, the graspable portion has an area of 1-4 mm^2. For some applications, cord 90 is looped through a part of the graspable portion (e.g., an opening 73), such that cord 90 is removably coupled to apparatus 20. For example, opening 73 through which cord 90 is looped may have a length of 0.5-1.2 mm, e.g., 0.8 mm, in at least one dimension.

Reference is now made to FIGS. 9-11. Typically, subsequently to inserting apparatus 20 into vitreous cavity 109, one or more tools are inserted into vitreous cavity 109. For example, a tool 200, e.g., a first grasping tool 220, is inserted into vitreous cavity 109 through opening 30 in posterior-segment scleral wall 1085. As shown in the cross section of eye 10 in FIG. 10, grasping tool 220, e.g., forceps 220, grasps apparatus 20. Typically, subsequently to grasping of apparatus 20 by first grasping tool 220, cord 90 is removed from eye 10. It is noted that for cases in which cord 90 is tied to apparatus 20, cord 90 is typically cut subsequently to apparatus 20 being grasped by first grasping tool 220.

For some applications, a second tool 210, e.g., a second grasping tool 230, is inserted into vitreous cavity 109 through second opening 32 in posterior-segment scleral wall 1085. As shown in the cross section of eye 10 in FIG. 11, grasping tool 230, e.g., forceps 230, grasps apparatus 20. It is noted that cord 90 may be removed following grasping of apparatus 20 by both first and second grasping tools 220 and 230, or following grasping of apparatus 20 by only first grasping tool 220.

Subsequently to grasping apparatus 20 by at least first grasping tool 220 (e.g., grasping apparatus 20 by only first grasping tool 220, or alternatively, by both grasping tools 220 and 230), apparatus 20 is rotated such that distal tips 26 of electrodes 23 point towards macula 1066 of eye 10 (FIG. 11).

Reference is now made to FIGS. 12 and 13. Subsequently to rotating, apparatus 20 is positioned on retina 106 in an epi-retinal position such that distal tips 26 of the electrodes 23 penetrate retina 106. Typically, positioning the apparatus in an epi-retinal position comprises positioning the apparatus using at least one of the first and the second grasping tools. For some applications, apparatus 20 is positioned on retina 106 using only one grasping tool, e.g., using first grasping tool 220. Alternatively, apparatus 20 is positioned on retina 106 using both first grasping tool 220 and second grasping tool 230 (as shown in FIG. 12).

For some applications, second tool 210 (or another tool (not shown)) comprises a non-grasping tool, e.g., a rod. In this case, apparatus 20 may be positioned on retina 106 using first grasping tool 220 to grasp apparatus 20, and using the non-grasping tool to push the electrodes of apparatus 20 into retina 106. For some applications, first grasping tool 220 is used to push the electrodes of apparatus 20 into retina 106 once apparatus 20 is positioned on the retina. As shown in FIG. 13, apparatus 20 is pressed against retina 106 using tool 220, in order to cause electrodes 23 of apparatus 20 to penetrate retina 106.

Reference is made to FIG. 14. For some applications, apparatus 20 is dropped onto retina 106, rather than being lowered all of the way onto the retina by tools 200 and 210. Typically, apparatus 20 is dropped onto retina 106 from at least 0.5 mm and/or less than 1.5 mm above the retina, e.g., from 1 mm above the retina. Apparatus 20 is dropped onto the retina such that apparatus 20 is positioned on the retina in an epi-retinal position and distal tips 26 of electrodes 23 penetrate retina 106. Typically, apparatus 20 has a density of 1.5-2 g/cc, which is typically greater than a density of 1.006-1.01 g/cc of the physiological solution (e.g., balanced salt solution (BSS)) present in vitreous cavity 109 thereby facilitating efficient but relatively slow dropping of apparatus 20. Generally, dropping apparatus 20 avoids possible damaging of apparatus 20 and/or retina 106 by accidently jiggling the apparatus or applying excessive pressure during the positioning of apparatus 20 using tools.

Figure 18:
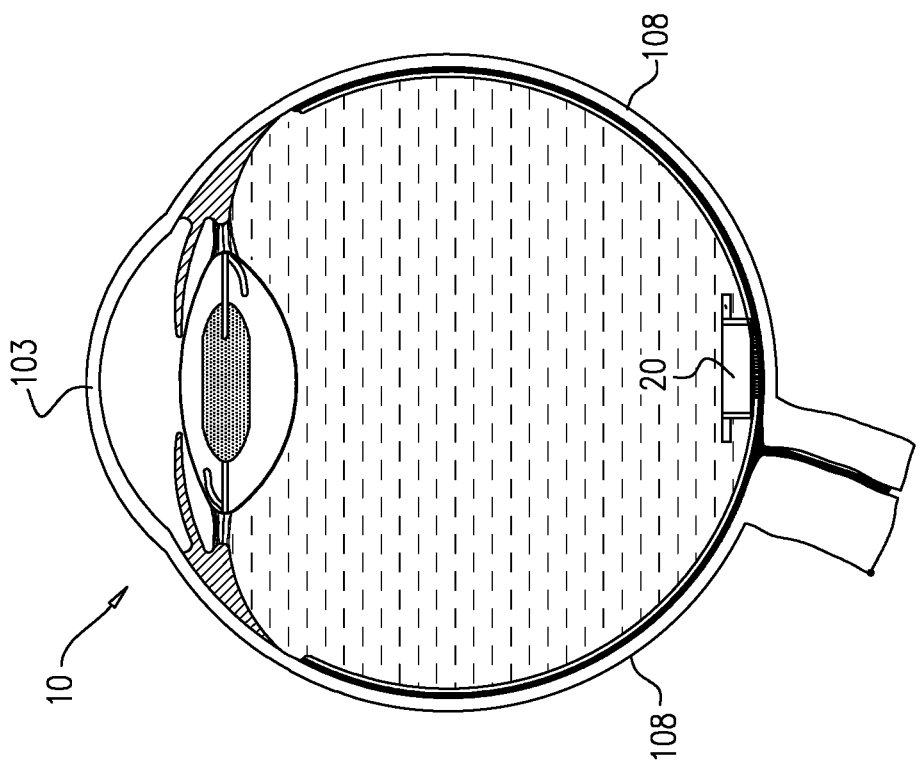
FIG. 18 is a schematic illustration of the eye following positioning of the apparatus on the retina of the subject in accordance with some applications of the present invention.
Figure 17:
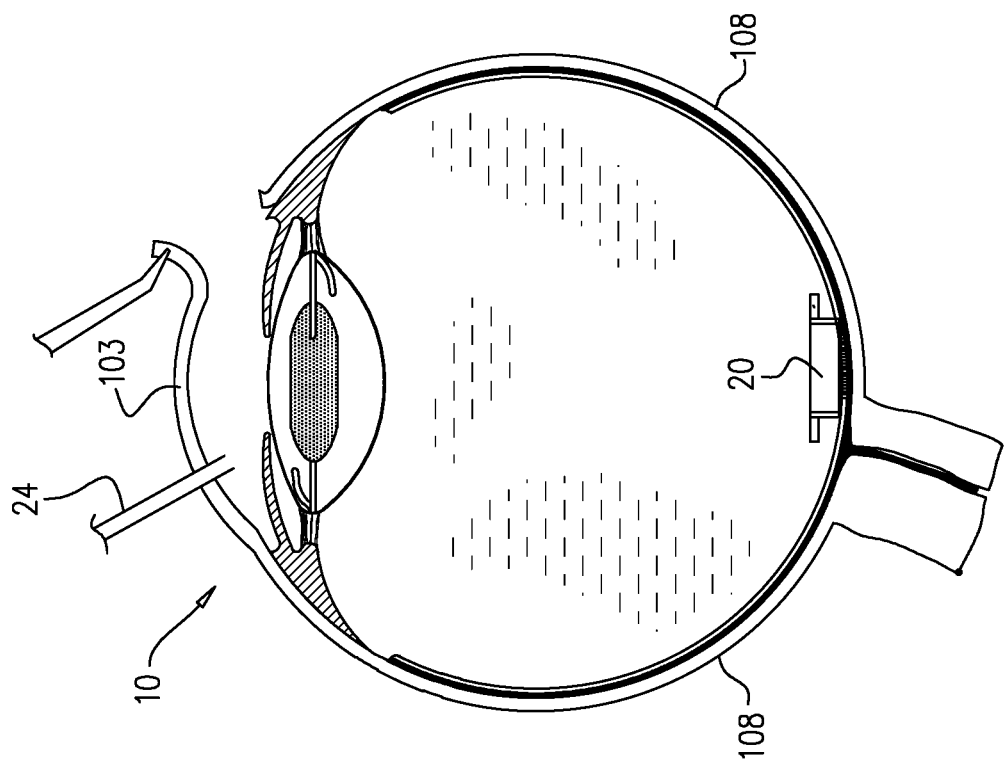

Reference is made to FIGS. 15-18. Following positioning of apparatus 20 onto retina 106, tools 200 and 210 are removed from eye 10 (FIG. 15), an intraocular lens 140 is inserted into eye 10 (FIGS. 16-17), and a fluid (e.g., balanced salt solution (BSS) or silicone oil) is used to fill the vitreous cavity (FIG. 18).

For some applications, techniques and apparatus described in the following patents and patent applications are combined with techniques and apparatus described herein:

U.S. Ser. No. 12/368,150 (issued as U.S. Pat. No. 8,150,526) to Gross et al.
U.S. Ser. No. 13/148,461 (issued as U.S. Pat. No. 9,265,945) to Gross et al., which is the US national stage of PCT/IL2010/000097 (WO 2010/089739).
U.S. Ser. No. 12/687,509 (issued as U.S. Pat. No. 8,718,784) to Gefen et al.
U.S. Ser. No. 12/852,218 (issued as U.S. Pat. No. 8,428,740) to Gefen et al.
U.S. Ser. No. 13/103,264 (issued as U.S. Pat. No. 8,442,641) to Gross et al.
U.S. Ser. No. 13/437,310 (issued as U.S. Pat. No. 8,706,243) to Gefen et al.
U.S. Ser. No. 14/199,462 (issued as U.S. Pat. No. 9,198,753) to Gefen et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   an array of stimulating electrodes configured for implantation in a retina of a subject's eye;
   circuitry configured to drive the electrodes to apply currents to the retina;
   a graspable portion coupled to the array and configured to facilitate positioning of the array in an epi-retinal position; and
   a cord removably coupled to the apparatus and (a) being not electrically coupled to the circuitry, and (b) looped through an opening of the graspable portion.

2. The apparatus according to claim 1, wherein the cord has a length of at least 3 cm.

3. The apparatus according to claim 1, wherein the graspable portion comprises a wire frame.

4. The apparatus according to claim 1, wherein the cord is looped through the opening of the graspable portion by being tied to the portion of the graspable portion.

5. The apparatus according to claim 1,
   wherein the graspable portion is a first graspable portion and the opening is a first opening, and
   wherein the apparatus further comprises a second graspable portion, which is (a) disposed on an opposite side of the apparatus from the first graspable portion, (b) coupled to the array and configured to facilitate positioning of the array in the epi-retinal position, and (c) shaped so as to define a second opening.

6. The apparatus according to claim 5, wherein the cord is removably coupled to the apparatus by being looped through only the first opening of the first graspable portion.

7. The apparatus according to claim 1, wherein the graspable portion comprises a rim of the apparatus.

8. A method comprising:
   inserting apparatus into a vitreous cavity of an eye of a subject while a cord is removably coupled to the apparatus, such that at least one end of the cord is disposed outside the subject's eye, the apparatus configured for implantation on a retina of the subject, and having (i) an electrode array including a plurality of stimulating electrodes shaped to define distal tips protruding from the array, (ii) a plurality of photosensors, and (iii) driving circuitry, configured to drive the electrodes to apply currents to the retina, wherein the cord is not electrically coupled to the circuitry;
   decoupling the cord from the apparatus and removing the cord from the subject's eye; and
   thereafter, positioning the apparatus in an epi-retinal position such that the distal tips of the electrodes penetrate the retina.

9. The method according to claim 8, wherein inserting the apparatus into the vitreous cavity comprises using the at least one end of the cord disposed outside the subject's eye to provide control of the apparatus.

10. The method according to claim 9, wherein using the at least one end of the cord disposed outside the subject's eye to provide the control of the apparatus comprises using the at least one end of the cord disposed outside the subject's eye to provide the control of the apparatus without holding the apparatus in place with graspers.

11. The method according to claim 9, wherein using the at least one end of the cord disposed outside the subject's eye to provide the control of the apparatus comprises using the at least one of the at least one end of the cord disposed outside the subject's eye to prevent the apparatus from falling onto the retina.

12. The method according to claim 8, wherein inserting the apparatus while the cord is removably coupled to the apparatus comprises inserting the apparatus while the cord is looped through an opening of a graspable portion of the apparatus, the graspable portion coupled to the array and configured to facilitate positioning of the array in the epi-retinal position.

13. The method according to claim 12,
   wherein the method further comprises subsequently to the inserting, grasping, using a grasping tool, the apparatus at the graspable portion, and
   wherein positioning the apparatus in the epi-retinal position comprises positioning the apparatus using the grasping tool.

14. The method according to claim 13, wherein decoupling and removing the cord from the subject's eye comprises decoupling and removing the cord from the subject's eye after grasping the apparatus by the grasping tool.

15. The method according to claim 14, wherein decoupling and removing the cord from the subject's eye comprises decoupling and removing the cord from the subject's eye (a) after grasping the apparatus by the grasping tool and (b) before positioning the apparatus in the epi-retinal position.

16. The method according to claim 12, wherein the graspable portion includes a wire frame.

17. The method according to claim 12,
   wherein the cord is looped through the opening of the graspable portion by being tied to the portion of the graspable portion, and
   wherein decoupling the cord from the apparatus comprises cutting the cord.

18. The method according to claim 12,
   wherein the graspable portion is a first graspable portion and the opening is a first opening, and
   wherein the apparatus further includes a second graspable portion, which is (a) disposed on an opposite side of the apparatus from the first graspable portion, (b) coupled to the array and configured to facilitate positioning of the array in the epi-retinal position, and (c) shaped so as to define a second opening.

19. The method according to claim 12, wherein the graspable portion includes a rim of the apparatus.

20. The method according to claim 8, further comprising:
   subsequently to inserting the apparatus, inhibiting advancement of the cord into the eye by tying the cord outside the eye; and
   untying the cord prior to the positioning of the apparatus in the epi-retinal position.

\* \* \* \* \*